(12) United States Patent
Koch et al.

(10) Patent No.: US 10,638,949 B2
(45) Date of Patent: May 5, 2020

(54) SYSTEM AND APPARATUS FOR ASSESSING METALLOSIS USING MAGNETIC RESONANCE IMAGING

(71) Applicants: New York Society for the Ruptured and Crippled Maintaining the Hospital for Special Surgery, New York, NY (US); Medical College of Wisconsin, Milwaukee, WI (US)

(72) Inventors: Kevin Matthew Koch, Wauwatosa, WI (US); Matthew F. Koff, Livingston, NJ (US); Hollis Potter, Greenwich, CT (US)

(73) Assignees: New York Society for the Ruptured and Crippled Maintaining the Hospital for Special Surgery, New York, NY (US); Medical College of Wisconsin, Milwaukee, WI (US)

( * ) Notice: Subject to any disclaimer, the term of this patent is extended or adjusted under 35 U.S.C. 154(b) by 146 days.

(21) Appl. No.: 15/494,191

(22) Filed: Apr. 21, 2017

(65) Prior Publication Data
US 2017/0307709 A1 Oct. 26, 2017

Related U.S. Application Data

(60) Provisional application No. 62/326,599, filed on Apr. 22, 2016.

(51) Int. Cl.
*A61B 5/055* (2006.01)
*G01R 33/565* (2006.01)
(Continued)

(52) U.S. Cl.
CPC ............ *A61B 5/055* (2013.01); *A61B 5/4528* (2013.01); *G01R 33/243* (2013.01); *G01R 33/56* (2013.01); *G01R 33/56536* (2013.01)

(58) Field of Classification Search
CPC .................. A61B 5/055; A61B 5/4528; G01R 33/56536; G01R 33/243; G01R 33/56
See application file for complete search history.

(56) References Cited

U.S. PATENT DOCUMENTS 7,821,264 B2 * 10/2010 Koch .................... G01R 33/243
324/307
7,952,356 B2 * 5/2011 Koch ............... G01R 33/56563
324/309
(Continued)

OTHER PUBLICATIONS

K.M. Koch, et al., "Imaging Near Metal with a MAVRIC-SEMAC Hybrid", Magnetic Resonances in Medicine, 65:71-82 (2011).
(Continued)

*Primary Examiner* — Dixomara Vargas
(74) *Attorney, Agent, or Firm* — Fish & Richardson P.C.

(57) ABSTRACT

A method includes: accessing MRI data acquired from a joint area, the MRI data including a series of spatially mapped spectral data points; generating MRI images of the joint area; receiving information encoding a region of interest that encompasses a suspected metal particle deposition area over at least one of the MRI images; constructing magnetic field maps using the MRI data, each representing off-resonance frequency shifts over the joint area; removing a background of off-resonance field inhomogeneity from the magnetic field map such that the region of interest is free from off-resonance field inhomogeneity; identifying clusters from the magnetic field maps with the background of off-resonance field inhomogeneity removed, the clusters defined over a first dimension of offset frequencies and a second dimension of cluster volumes; and computing a quantitative metric by combining information from the identified clusters according to both the first dimension and the second dimension.

20 Claims, 9 Drawing Sheets

(51) Int. Cl.
*G01R 33/24* (2006.01)
*G01R 33/56* (2006.01)
*A61B 5/00* (2006.01)

(56) References Cited

U.S. PATENT DOCUMENTS

| | | | | |
|---|---|---|---|---|
| 8,274,286 B2* | 9/2012 | Koch | ................... | G01R 33/243 |
| | | | | 324/300 |
| 8,421,459 B2* | 4/2013 | Koch | ................... | G01R 33/243 |
| | | | | 324/300 |
| 9,678,190 B2* | 6/2017 | Koch | ............... | G01R 33/56536 |
| 9,989,613 B2* | 6/2018 | Wiens | ............... | G01R 33/56536 |
| 2009/0184711 A1* | 7/2009 | Koch | ................... | G01R 33/243 |
| | | | | 324/307 |
| 2010/0308827 A1* | 12/2010 | Koch | ................... | G01R 33/243 |
| | | | | 324/309 |
| 2010/0308828 A1* | 12/2010 | Koch | ................... | G01R 33/243 |
| | | | | 324/312 |
| 2011/0103670 A1* | 5/2011 | Koch | ................... | G01R 33/243 |
| | | | | 382/131 |
| 2013/0265046 A1* | 10/2013 | Koch | ............... | G01R 33/56536 |
| | | | | 324/309 |
| 2016/0154080 A1* | 6/2016 | Wiens | ............... | G01R 33/56536 |
| | | | | 324/309 |
| 2018/0292491 A1* | 10/2018 | Koch | ....................... | G01V 3/14 |

OTHER PUBLICATIONS

K.M. Koch, et al., "A Mechanism for Quantifiable MRI-Based Detection of Cobalt-Chromium Particulate Deposits Near Total Hip Replacements", Proc. Int'l. Soc. Mag. Reson. Med. 23 (2015).
G. Labek, et al., "Revision Rates After Total Joint Replacement", The Journal of Bone & Joint Surgery, vol. 93-B, No. 3, Mar. 2011.
T. Liu, et al., "A Novel Background Field Removal Method for MRI Using Projection Onto Dipole Fields (PDF)", NMR Biomed, 2011; 24: 1129-1136.
S.S. Rajaee, et al., "Spinal Fusion in the United States", Spine vol. 37, No. 1, pp. 67-76.

\* cited by examiner

SYSTEM AND APPARATUS FOR ASSESSING METALLOSIS USING MAGNETIC RESONANCE IMAGING

CROSS REFERENCE TO RELATED APPLICATIONS

This application claims benefit of U.S. provisional Patent Application 62/326,599, filed Apr. 22, 2016, which is hereby incorporated by reference in its entirely.

STATEMENT AS TO FEDERALLY SPONSORED RESEARCH

This invention was made with government support R01 AR064840 awarded by the National Institutes of Health. The government has certain rights in the invention.

TECHNICAL FIELD

This description generally relates to magnetic resonance imaging (MRI).

BACKGROUND

MRI provides soft-tissue images with superior contrast. Thus, MRI has become a widely-used modality for joint imaging.

SUMMARY

In one aspect, some implementations provide a method for determining metallic particle deposition in tissues near metallic implants using magnetic resonance imaging (MRI) data, the method including: accessing MRI data acquired from a joint area that has received a replacement implant, the MRI data including a series of spatially mapped spectral data points, each at a particular offset frequency; generating MRI images of the joint area from the MRI data; receiving information encoding a region of interest that encompasses a suspected metal particle deposition area over at least one of the MRI images generated from the MRI data; constructing magnetic field maps using the MRI data, each magnetic field map representing off-resonance frequency shifts over the joint area; removing a background of off-resonance field inhomogeneity from the magnetic field map such that the region of interest is free from off-resonance field inhomogeneity caused by the implant itself; identifying clusters from the magnetic field maps with the background of off-resonance field inhomogeneity removed, the clusters defined over a first dimension of offset frequencies and a second dimension of cluster volumes; and computing a quantitative metric by combining information from the identified clusters according to both the first dimension and the second dimension.

Implementations may include one or more of the following features.

The MRI data may include a series of three-dimensionally encoded spectral volumes, each spectrum volume corresponding to a particular offset frequency, and the spectrum volumes acquired with overlapping offset frequencies. The MRI data may include a series of two-dimensionally encoded spectrum slice sets, each spectrum slice set corresponding to a particular offset frequency, and the spectrum slice sets acquired with overlapping offset frequencies.

Constructing the magnetic field maps may include: constructing the magnetic field maps by fitting the series of spatially mapped spectral data points against a model that describes the radiofrequency spectral profile applied when acquiring the MRI data. Fitting the series of spectral data points may include: fitting spectral profiles of each spatial quantum of the series of spatially mapped spectral data points against the model, the model including parameters that includes an offset frequency for each pixel of the constructed magnetic field map. Constructing the magnetic field maps may be based on a difference in phase information from the MRI data acquired with different echo times.

The method may further include: forming a tissue mask by examining a spectral integrity of the series of spatially mapped spectral data points to determine spatial areas that correspond to tissue. Examining the spectral integrity of the series of spatially mapped spectral data points may include: quantifying the spectral integrity by computing a ratio of a cumulative highest magnitude of a first number of spectrum volumes to a sum of a second number of spectrum volumes, wherein the first number and the second number jointly represent a total number of the spectrum volumes.

The method may additionally include: applying the tissue mask to the magnetic field maps prior to removing the background of background of off-resonance field inhomogeneity.

Computing the quantitative metric may include applying a nonlinear weighting to sum information from the clusters in both the first dimension and the second dimension. Computing the quantitative metric may include applying a linear weighting to sum information from the clusters in both the first dimension and the second dimension.

In another aspect, some implementations provide a system for determining metallic particle deposition in tissues near metallic implants using magnetic resonance imaging (MRI) data, the system including: an MRI scanner system configured to acquire MRI data from a joint area that has received a replacement implant, the MRI data including a series of spatially mapped spectral data points, each at a particular offset frequency; a data processing system in communication with the MRI scanner system, the data processing system comprising at least one processor configured to perform the operations of: accessing the MRI data acquired from the joint area; generating MRI images of the joint area from the MRI data; receiving information encoding a region of interest that encompasses a suspected metal particle deposition area over at least one of the MRI images generated from the MRI data; constructing magnetic field maps using the MRI data, each magnetic field map representing off-resonance frequency shifts over the joint area; removing a background of off-resonance field inhomogeneity from the magnetic field map such that the region of interest is free from off-resonance field inhomogeneity caused by the implant itself; identifying clusters from the magnetic field maps with the background of off-resonance field inhomogeneity removed, the clusters defined over a first dimension of offset frequencies and a second dimension of cluster volumes; and computing a quantitative metric by combining information from the identified clusters according to both the first dimension and the second dimension.

Implementations may include one or more of the following features.

The MRI data may include a series of three-dimensionally encoded spectral volumes, each spectrum volume corresponding to a particular offset frequency, and the spectrum volumes acquired with overlapping offset frequencies. The MRI data may include a series of two-dimensionally encoded spectrum slice sets, each spectrum slice set corresponding to a particular offset frequency, and the spectrum slice sets acquired with overlapping offset frequencies.

Constructing the magnetic field maps may include: constructing the magnetic field maps by fitting spatially mapped spectral data points against a model that describes the radiofrequency spectral profile applied when acquiring the MRI data. Fitting the series of three-dimensionally encoded spectral volumes may include: fitting spectral profiles of each spatial quantum of the series of spatially mapped spectral data points against the model, the model comprising parameters that includes an offset frequency for each pixel of the constructed magnetic field map.

Constructing the magnetic field maps may be based on a difference in phase information from the MRI data acquired with different echo times.

The data processing system may be configured to perform the operations of: forming a tissue mask by examining a spectral integrity of the series of spatially mapped spectral data points to determine spatial areas that correspond to tissue.

Examining the spectral integrity of the series of spatially mapped spectral data points may include: quantifying the spectral integrity by computing a ratio of a cumulative highest magnitude of a first number of spectrum volumes to a sum of a second number of spectrum volumes, wherein the first number and the second number jointly represent a total number of the spectrum volumes.

The data processing system may be configured to perform the operations of: applying the tissue mask to the magnetic field maps prior to removing the background of background of MRI field inhomogeneity. Computing the quantitative metric may include applying a nonlinear weighting to sum information from the clusters in both the first dimension and the second dimension. Computing the quantitative metric may include applying a linear weighting to sum information from the clusters in both the first dimension and the second dimension.

The details of one or more aspects of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Embodiments will now be described, by way of example only, with reference to the drawings, in which:

FIGS. 3A to 3B show a zoomed image of the field map of FIG. 2 within an identified region of interest, as well as a residual tissue off-resonance map from the same identified region of interest and with background field-suppressed.

Like reference symbols in the various drawings indicate like elements.

DETAILED DESCRIPTION

Joint replacement is commonly practiced for functional improvements of a human joint. The replacements may include implants made of polyethylene or metal. Wear-induced tear may develop over the articulating surfaces of these replacement implants. Load conditions may exacerbate the tear, which may accelerate once initiated. In many cases, the tear includes the development of local debris. Adverse local tissue reactions (ALTRs) may be caused by a direct toxic effect when high levels of wear debris or ions are generated. The ALTRs may also be caused by an immune reaction often attributed to type-IV delayed type allergic hypersensitivity. Histologic studies of ALTRs show soft tissues with patterns of diffuse and perivascular infiltration of T and B lymphocytes, accumulation of plasma cells, and necrosis.

Early detection of ALTRs and an expedited revision of, for example, a total hip replacement may be crucial to achieve successful clinical outcome and minimize operative and rehabilitation costs. Revisions of hip resurfacing arthroplasty patients with an ALTR tend to have longer operative times, more surgical complications, and worse measures of clinical outcome than revision of traditional metal-on-polyethylene implants. In general, difficult revision surgeries have 63% higher operative costs and 27% higher rehabilitation costs, as may be found for ALTR patients. Once an ALTR has been identified and revision surgery is elected, the length of hospital stay and the amount of hospital charges are expected to be reduced, by as much as 39% and 22%, respectively. It has been shown that elective revision hip arthroplasty surgeries may have saved $131.8 million in 2005, and may save as much as $560 million in 2030.

In this context, a non-invasive means to monitor the progression of the wear and tear associated with joint replacement by quantitatively tracking, for example, metal debris deposition would be advantageous. Metallic debris causes unique conditions compared to polymeric (plastic) debris because the metallic debris tend to cause increased risk for larger inflammatory response or tissue reaction. Total hip replacement, for example, may have failure rates of 6% and 13% at 5 and 10-year benchmarks, which can be related to metallic debris deposition from installed implant components. Most often, metallic debris particles are composed of cobalt-chromium alloys, which have a strong paramagnetic magnetic susceptibility relative to biological materials. On MRI, however, it is difficult to distinguish polymeric from metallic deposits while joint replacement can include implants made of metal and polyethylene. For example, both polymeric debris and metallic debris appear as lower signal regions on proton-density or T1 weighted images. While in cases of symptomatic total hip replacements it may be possible to identify debris based on magnitude MRI data, it remains clinically advantageous to differentiate metallic debris from polymeric debris.

This disclosure describes system and methods developed to capture MRI signals indicative of metallic debris. In particular, some implementations leverage the off-resonance effect caused by the presence of metal debris to capture spatially resolved signals spectrally away from the Larmor frequency of protons in the main magnet of the MRI scanner system. In some instances, the intensity values and the corresponding offset frequency values of signals from a particular locale are analyzed in a quantitative manner. In one example, a quantitative metric is generated by the non-invasive approach based on MRI. Comparison of this quantitative metric with histology results can lead to a strong correlation. In particular, the regional quantitative metric disclosed herein is shown to statistically correlate with local histology metallosis scores in subjects undergoing total hip revision surgery. This statistically significant correlation demonstrating the utility of this example quantitative metric as well as the potential of the non-invasive MRI approach disclosed herein.

Figure 1:
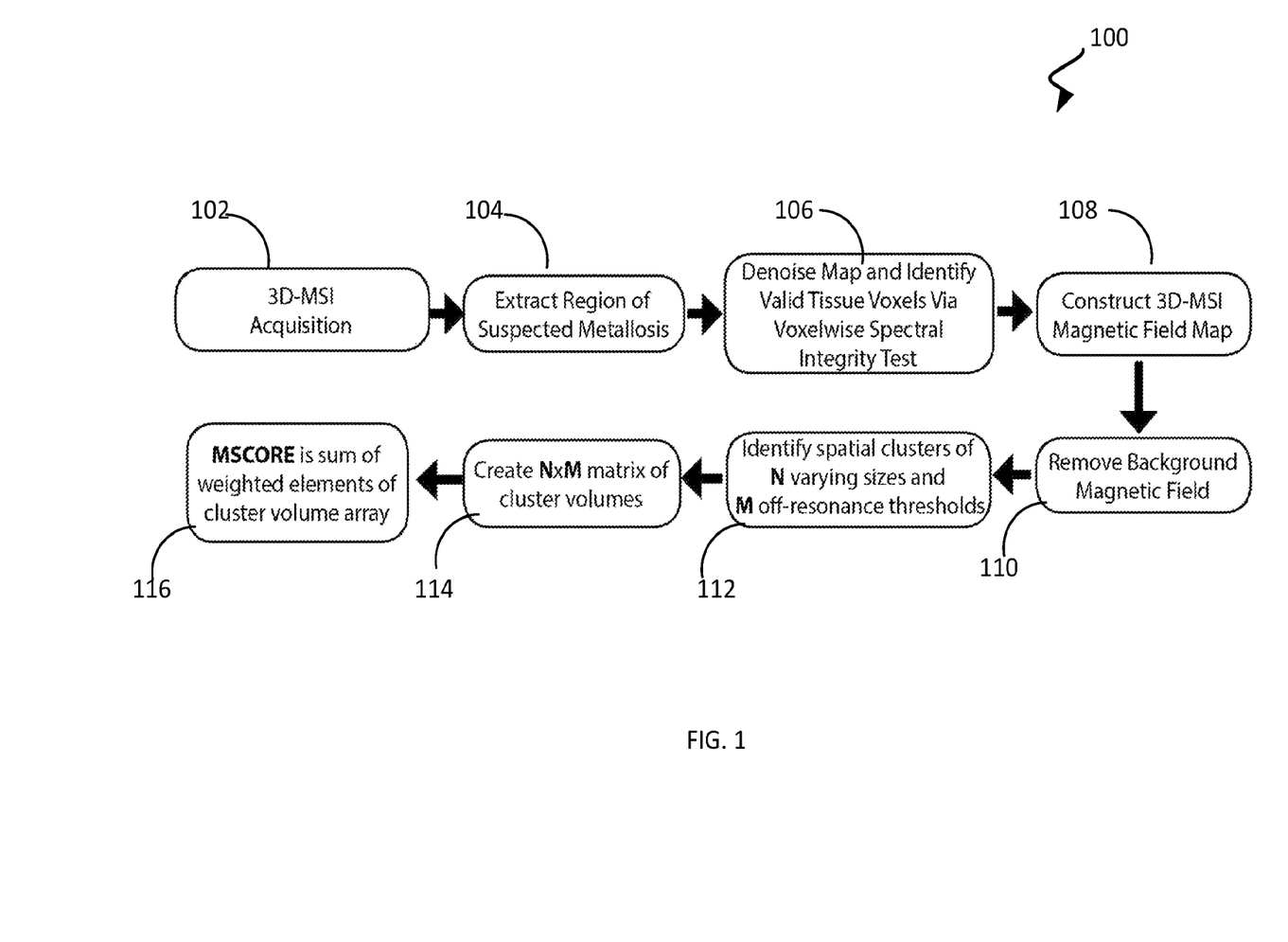
FIG. 1 shows an example of a flow chart to compute a quantitative metric to evaluate metallosis based on magnetic resonance imaging (MRI) data.

FIG. 1 shows an example of a flow chart 100 to compute a quantitative metric to evaluate metallosis based on magnetic resonance imaging (MRI) data. Initially, a patient with joint replacement implant is placed inside the bore of a magnet of an MRI scanner system and a 3-dimensional multi spectral imaging (3-D MSI) MRI data is acquired from the joint area of the patient (102). The 3-D MSI is one example of imaging methods to identify a specific physical characteristic parameter at each pixel in an MRI image. In this example, multiple data sets from the same spatial volume may be generated, each data set corresponding to a particular offset frequency from the Larmor frequency of protons in the magnet of the MRI scanner system. For illustration, data sets corresponding to offset frequencies from −10 kHz to +10 kHz may be obtained, each data set encoding MRI imaging data with a slightly varying center frequency around the Larmor frequency. In this illustration, the spatial slice of the patient's joint may be selected by a judicious combination of slice selecting radio-frequency (RF) pulses and associated gradient pulses such that only one spatial slice is selected by transmitting the RF pulses. The received signals, however, can include off-resonance signals due to the presence of metallic debris. The received signals may be classified into different bins, each corresponding to a particular offset frequency. In this manner, MRI data sets from multiple offset frequency may be obtained accordingly. An example of the MRI imaging sequence to capture the multi-spectral data is the Multi-Acquisition with Variable Resonance Image Combination (MAVRIC) 3D-MSI implementation that utilizes overlapping Gaussian spectral windows such that the offset frequencies in neighboring spectral locations overlap.

The acquired 3D-MSI data may be reconstructed to reveal the anatomical details. Further referring to FIG. 2A, an example of the anatomical image (202) from a 3D-MSI data set is shown. In this illustration, a MAVRIC SL imaging sequence is used, same as the one used for FIG. 6 and FIG. 7. Image acquisition parameters may be as follows: coronal scan plane, 36-40 cm field of view (FOV), 7 ms echo time (TE), 4 s repetition time (TR), echo train length (ETL) of 20, 5 mm slice thickness, (512×256×24–32) in-plane data matrix, 24 spectral bins, spectral width of 2.25 kHz (full-width-half maximum), and a 1 kHz spectral bin separation, with a receiver bandwidth of ±125 kHz (500 Hz/pixel). Other instances may use Slice Encoding for Metal Artifact Correction (SEMAC) sequences.

Figure 3A:
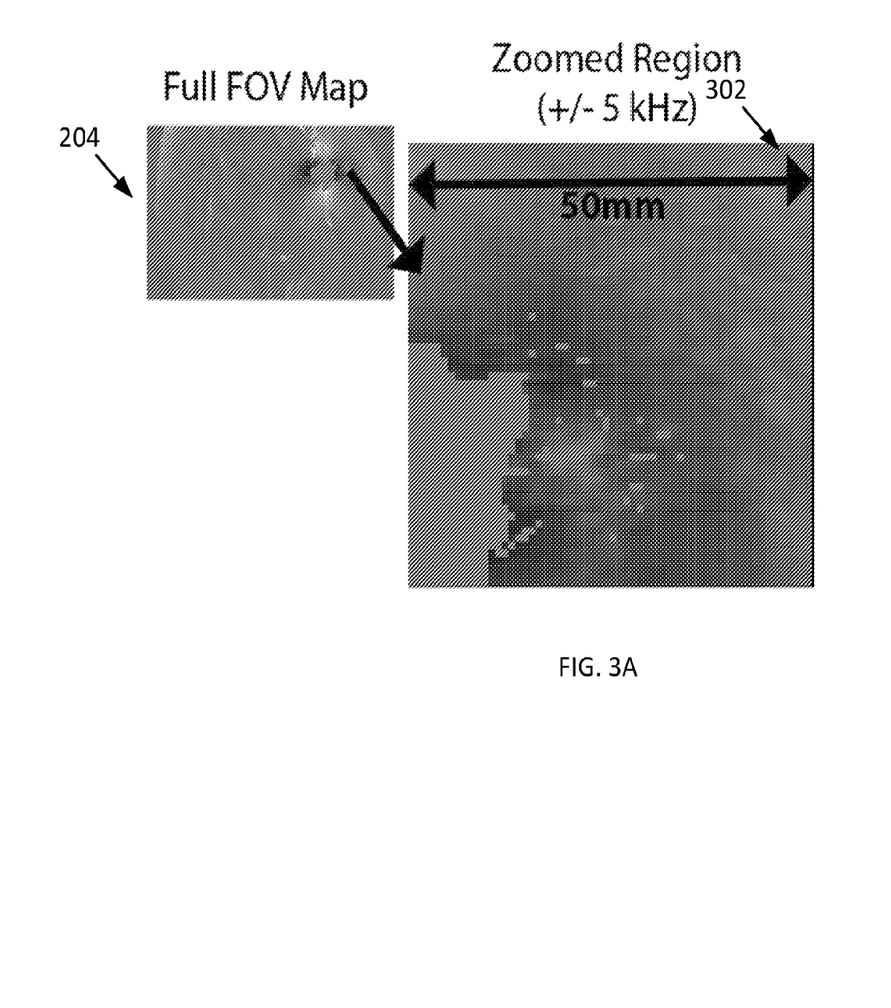
Figure 6A:
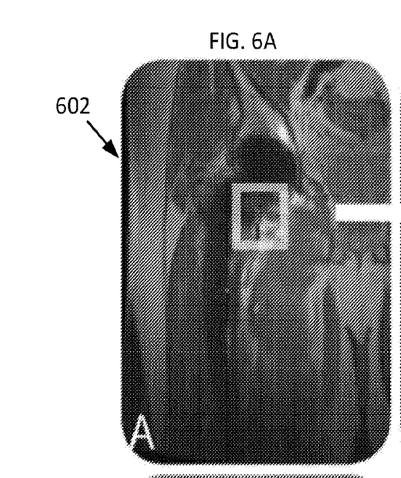
FIG. 6A to FIG. 6F illustrate another example of computing the mScore and generating a fused mapping of metallosis.
Figure 6B:
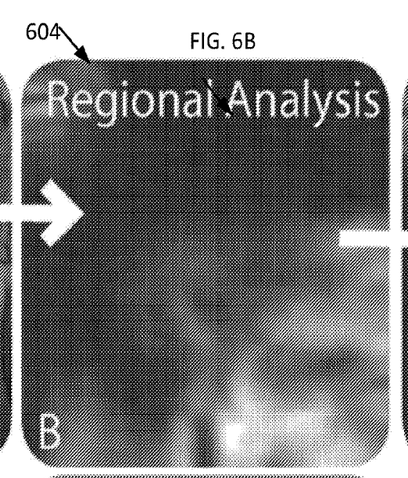
Figure 6C:
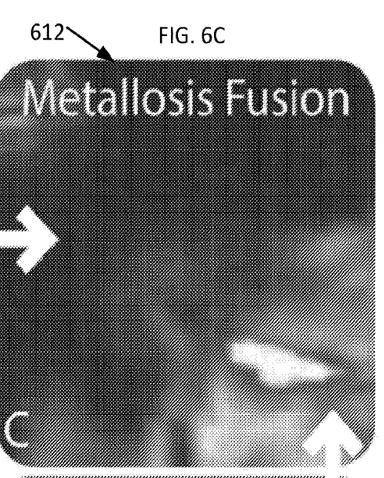

Based on the reconstructed anatomical image, regions of interest of suspected metallosis may be obtained (104). Here, an operator may specify the region of interest (ROI) that encompasses the suspected metallosis. As shown in FIGS. 3A and 6B, for each subject, a region of suspected metallosis was identified on a MAVRIC SL images by a board certified musculoskeletal radiologist with over decades of experience of interpreting MR images of arthroplasty. After the ROI has been selected, the 3D-MSI data set may be denoised and valid tissue voxels may be identified (106). In some instances, the valid tissue voxels may be identified through a voxelwise spectral integrity test. For example, tissue masks may be determined for each volume by examining the 3D-MSI spectral integrity at each voxel. In one illustration, a given voxel in the dataset may be expected to have 3 to 5 dominant spectral bin contributions, depending on the severity of local induction field gradients. In this illustrative example, spectral integrity can be quantified by computing the ratio of the cumulative of a first number of highest magnitude spectral bin signals to the sum of signals from a second number of spectral bins. When the total number of spectral bins are, for example, six, the first number can be three, and the second number can be three as well. A ratio of 3.0 has been empirically found to provide a reliable masking for the purposes of tissue masking. In a typical application, the implant region may be identified in this integrity mask by finding the largest contiguous region of poor spectral integrity (<3.0) in the volume. This "implant" volume can then dilate by, for example, an additional 3 mm to ensure high quality spectral signal is utilized in the analysis of remaining tissue regions. The cumulative goal of these pre-processing steps was to remove voxels that have poor MRI signal integrity from the off-resonance analysis. In these instances, voxels that correspond to non-tissue areas may not have sufficient signal-to-noise (SNR) ratio to undergo further analysis, for example, phase difference assessment, and may be dismissed from phase analysis. Thereafter, magnetic field map may be constructed.

Figure 2A:
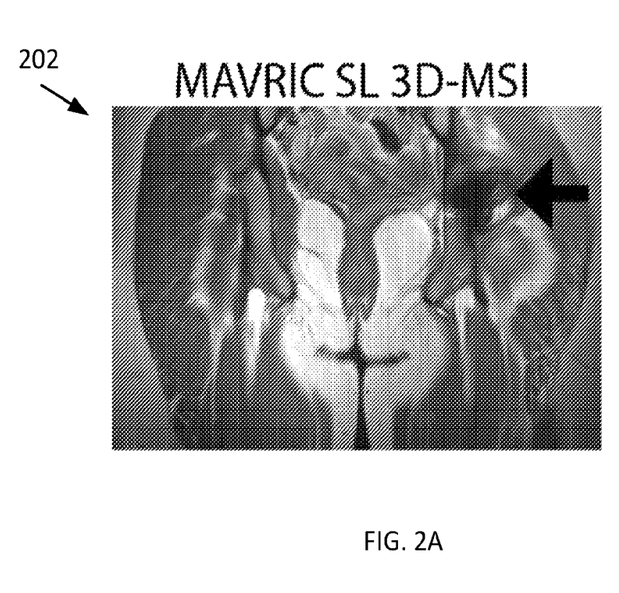
FIGS. 2A to 2B show examples of a representative image from a 3-D Multi-Spectral Imaging (MSI) MRI image data set as well as the corresponding field map for the representative image.
Figure 2B:
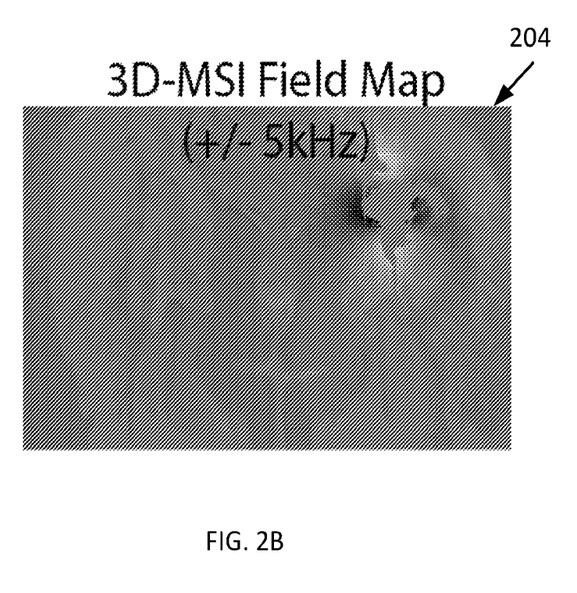

While the magnitude image (202) shows the anatomical structures of the joint in FIG. 2A, a field map (204) may be generated based on the 3D-MSI data set, as shown in FIG. 2B. In some instances, the MRI data set may include data acquired from Multi-Acquisition with Variable Resonance Image Combination (MAVRIC) 3D-MSI implementation that utilizes overlapping Gaussian spectral windows. In these instances, a magnetic field map can be constructed from the 3D-MSI data set (108). This 3D-MSI dataset can provide 3-5 spectral data points per image voxel which characterize this spectral windowing function. These spectral profiles can be approximated by the Gaussian model:

$$S_b(A, \Delta v, \sigma) = Ae^{-\frac{(\Delta v - v_b)^2}{2\sigma^2}}. \tag{1}$$

Figure 6D:
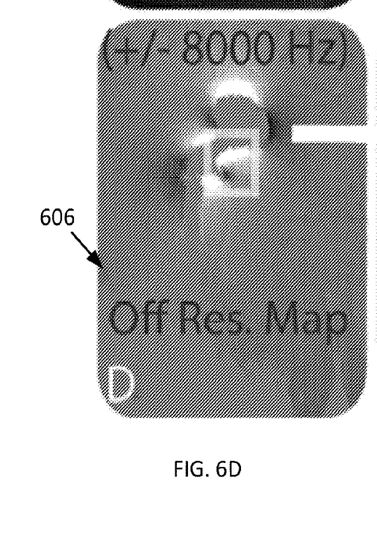
Figure 6E:
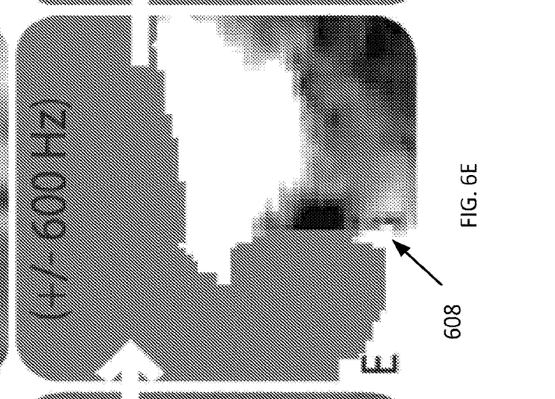
Figure 6F:
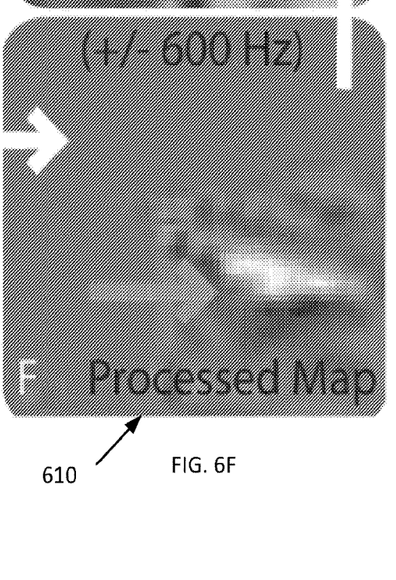

For each voxel in the image, acquired bin data can be fit to Eqn. 1 so as to identify the parameters A, $\Delta v$, and $\sigma$. This spectral profile is analytically differentiable, which readily enables parameter optimization at each voxel using iterative steepest descent approaches. Since this generalized approach performs a fit to an anticipated model within the MSI spectral domain, it is advantageously free from sensitivity to off-resonant bin noise and ghosting. In the example of FIG. 2B, the model-based field map 204 can be computed using an analytic steepest-descent iterative approach. The field map of FIG. 6D is likewise generated via this model-based approach.

The field map may include the background distortion caused by the presence of the metallic substance. The background can be removed (110), for example, from the region of interest being analyzed. A variety of background removal methods may be used, including, the Projection onto Dipole Fields (PDF) technique that performs an inversion of dipolar field "sources" within voxels labelled as "non-tissue" across the analyzed volume of interest. For the purposes of background removal, this PDF method can be well-suited to identify and remove the implant-induced field. In one sense, the implant can be well-approximated as a sum of high susceptibility source dipoles that sum to form the implant-induced perturbation field. Further referring to FIG. 3, a zoomed region 302 corresponding to the ROI is shown, along with the same zoomed region but with background removed (304).

A fundamental limit of particulate map detection stems from local fat-water chemical shifts, which are present in MSI-derived off-resonance maps. The presence of chemical shift contamination establishes an off-resonance detection threshold, below which particulate deposits cannot be distinguished from normal fat/water tissue transitions (225 Hz at 1.5 T).

Figure 4A:
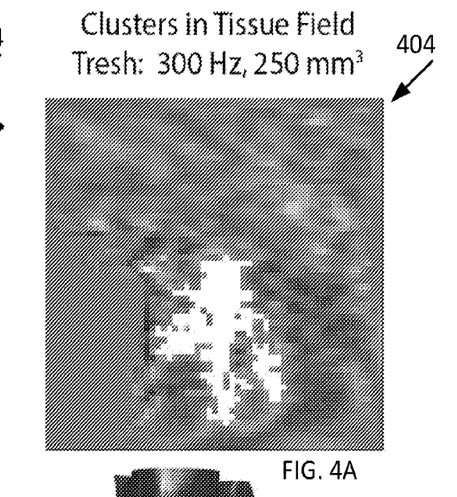
FIGS. 4A to 4C show the magnitude image corresponding to the residual tissue off-resonance map from FIG. 3, along with an example of a clusters identified with a threshold of 500 Hz offset and 250 mm voxel size as well as a 3D rendering the identified clusters in 3D.
Figure 4B:
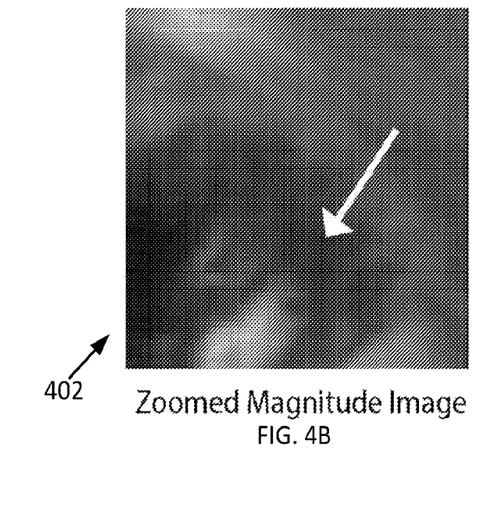
Figure 4C:
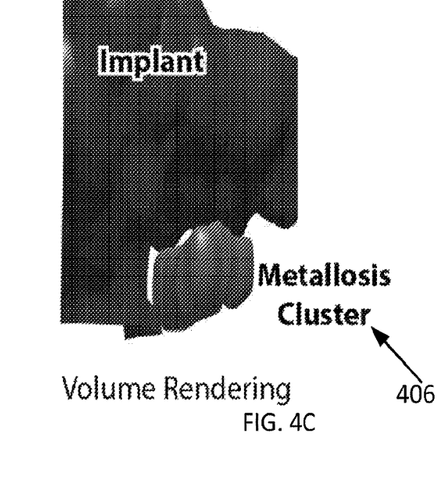

Based on the ROI with background removed, spatial clusters of N varying sizes and M off-resonance thresholds may be identified (112). In particular, FIG. 4 shows an example of a cluster being identified (404) for the ROI with background removed (304). Here, this particular cluster being identified corresponds to an offset frequency of 300 Hz and a volume of 250 mm$^3$. Magnitude image 402 for this cluster has a hypo-intense area, indicated by the white arrow, which correspond to the saturated region in example 404. This area corresponds the central focus of the suspected metallic debris pocket. Based on images 304, 404, and 402, volumetric surface rendering of the implant region and the metallosis cluster can be generated, as shown in image 406.

In this manner, clusters of field offsets can be identified at N levels of offsets, for example, 300 350 400 450 500 Hz, and M cluster volume thresholds, for example, 60/120,240, 360,480 mm$^3$. The volume of identified clusters at these settings forms an N×M matrix (114). After applying an exponential weighting to the matrix elements (which can be used to tighten mScores for a wide spectrum of metallosis severity), the elements are summed to form the mScore (116).

In one proof-of-concept demonstration, tissue samples (~1 cm$^3$) were extracted during revision surgery from regions of suspected particulate debris in pre-operative MRI. Histological scoring was performed on these samples, focusing on the Fujishiro metal particle score which ranges from 0 (no metal particles) to 4 (significant metal particles). Due to the uncertainty of precise sample locations extracted during surgery, a relatively large volume (120 cm$^3$) surrounding the indented extraction point was utilized for mScore analysis. The example demonstrated in FIGS. 2-4 resulted in a computed mScore of 21 and had a Fujishiro metallosis histology score of 4/4. This demonstration may indicate that there can be a correlation between the histology analysis and the mScore, if the sample locations match.

Figure 5:
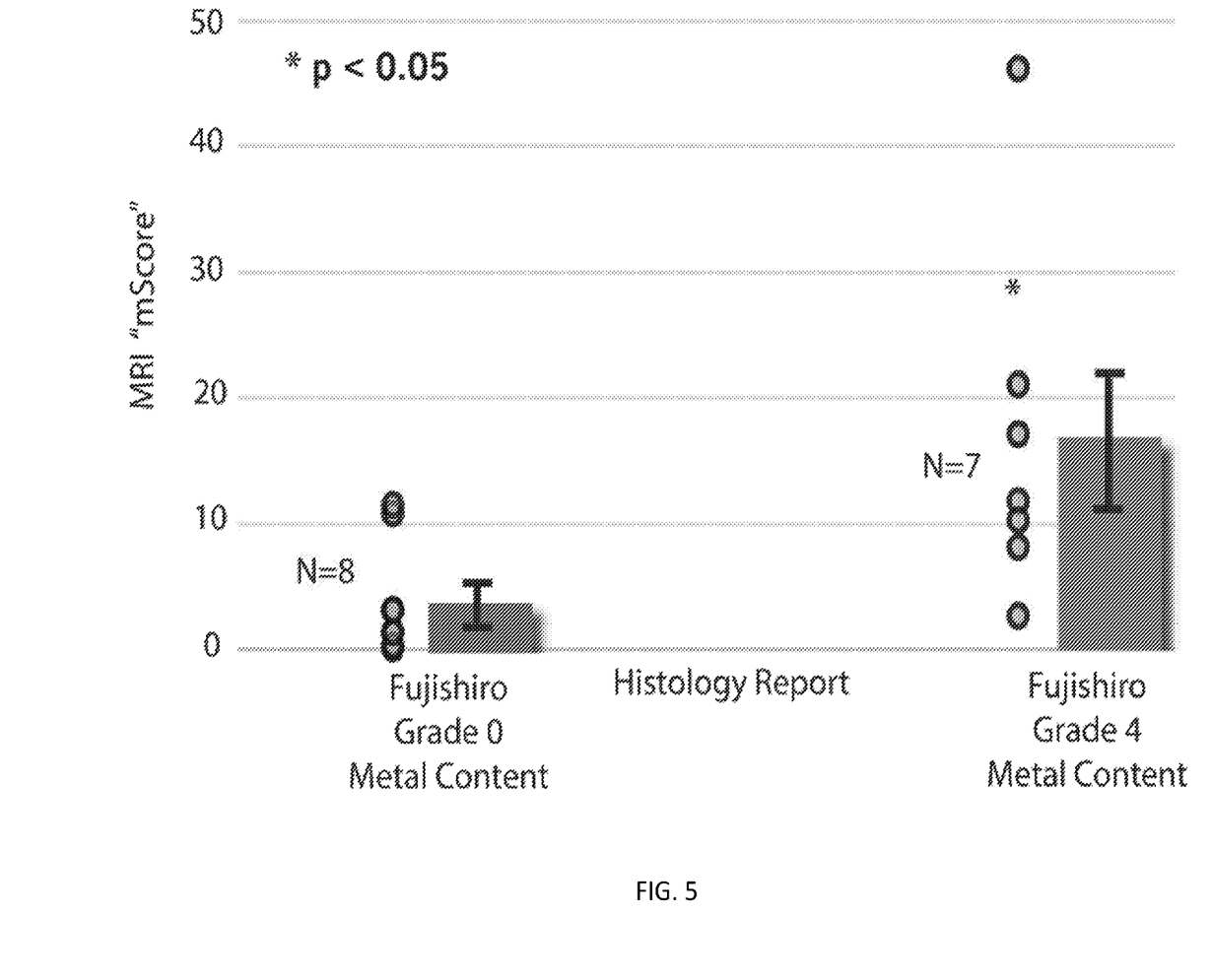
FIG. 5 compares examples of the computed quantitative score with histology readout, indicating a statistically significant correlation.

FIG. 5 presents the cohort mScore against histology analysis. In a cohort of 15 subjects undergoing total hip revision surgery, regional mScores were computed using pre-operative 3D-MSI imaging data and then correlated with histological metallosis scores from local tissue samples retrieved during surgery. Referring to FIG. 1, based on this regional identification from 104, the regional identification may be used to guide extraction of a 1 cm$^3$ tissue sample during the surgical revision procedure. These regions may be denoted as areas of low signal intensity within the synovial envelope on the MAVRIC SL images. Extracted samples can be fixed in formalin, processed for routine histology, and representative sections were graded by a board-certified pathologist with more than decades of experience specializing in orthopaedic pathology and biomaterials. The utilized histological metallosis metrics have previously been described by Fujishiro and Willert. Briefly, these evaluation methods semi-quantitatively grade the presence and extent of histiocytes, particle types, and tissue particle load under high magnification (400×). Tissues were also evaluated using Campbells ALVAL (aseptic lymphocytic vasculitis associated lesion) score. The Fujishiro null-valued group exhibits a tight clustering of low mScores, while the Fushishiro 4/4 valued group has a much broader spread of scores, with a much higher mean. The relatively broad distribution of mScores within the two Fujishiro groups may indicative of the large systematic uncertainties. While localizing a small tissue sample extraction during surgery on the MRI images (for mScore analysis) can present substantial logistical difficulties (e.g., the metallosis pockets detected in the larger mScore analysis volumes may be missed during histological tissue extraction), the results provides proof that the mScore has inherent diagnostic and prognostic value, just like the traditional histology analysis. Indeed, the two observables correlated well with one another. A Wilcox/Ranked-Sum analysis of the cohort yielded a p-value of 0.025, as shown in FIG. 5. This strong statistical correlation demonstrates that the presented methods offer a promising potential MRI-based biomarker for metallosis assessment near total hip arthroplasty. The mScores shows more variance than histology results from the tissue samples. This is attributable to the more quantitative and likely more sensitive analyses that become feasible using the full MRI dataset.

FIGS. 6 to 9 illustrate more examples of the mScore computing process. FIG. 6A shows the large field of view multi-spectral images (MSI) while FIG. 6D shows the off resonance map from the same large field of view. After application of the region of interest (ROI), the extracted image is shown in FIG. 6B. Voxel-wise 3D-MSI MR data for the corresponding region is then used to construct an off-resonance map shown in FIG. 6E. Background extraction using the PDF method then exposes the local tissue off-resonance distribution, as shown in FIG. 6F, which is then fused with FIG. 6B to generate the metallosis fusion image of FIG. 6C. In particular, FIG. 6C reveals the suspected metallosis after thresholded cluster analysis. In the examples from FIGS. 6 to 9, the mScores were computed using off-resonance thresholds of Ti=[350 400 450 500 550 600] Hz and cluster size thresholds of Sj=[0.3 0.6 1.2 1.8 2.4] cm$^3$. The choice of a minimum off-resonance threshold of 350 Hz can provide a conservative buffer above the chemical shift threshold, so as to reduce false-postive detection. Clusters can be identified using the spatially-correlated 3dclust algorithm provided by the AFNI toolbox.

Given a cluster size array Ci,j, mScores were computed according to:

$$mScore = \sum_{i,j} e^{-(T_i + \alpha S_j)} C_{i,j}, \quad (2)$$

where α can be used to balance the weighting between Ti and Sj. Data shown in FIGS. 6-9 used an empirically chosen value of α=160. In addition to regions of suspected metallosis, mScore analysis was also performed for 16 of the 27 subjects in soft tissue regions where no metallosis would reasonably be expected. For subjects with unilateral hip replacements, these regions were identified on the opposing hip joint. Subjects with bilateral hip replacements had control volumes identified from lower regions on the distal femoral stem outside of the femoral cortex, where metallosis is less likely to be identified. This control analysis may serve to assess a false-positive incidences of the disclosed methods.

Figure 7:
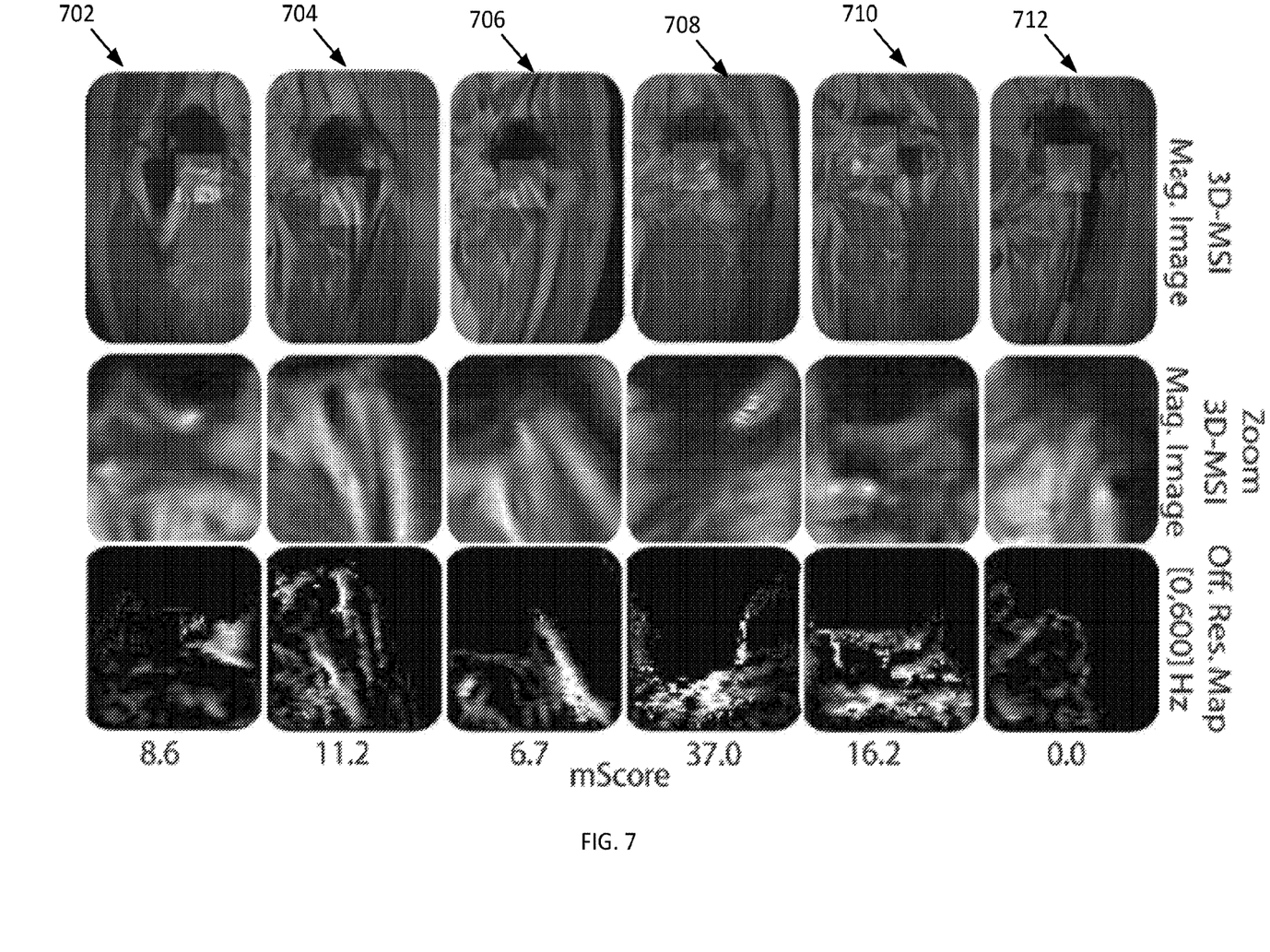
FIG. 7 highlights case studies for six (6) symptomatic subjects with suspected metallosis, displayed in six respective columns.

FIG. 7 shows the mScore computing processes for a cohort of six (6) symptomatic subjects. In each column, the top graph shows the magnitude image from the 3D-MSI MR data; the central graph shows the zoomed magnitude image from the 3D-MSI data corresponding to the region of interest (ROI); and the bottom row shows localized background removed off-resonance maps (bottom row) with computed mScores. Clear regions of locally isolated positive off-resonance are seen in all cases, which translates to mScores of various amplitudes depending on the 3-dimensional size and off-resonance amplitude of the pockets.

Figure 8A:
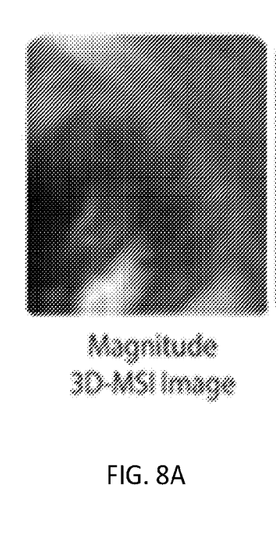
FIG. 8A to FIG. 8D illustrate the comparison between two off-resonance mapping methods.
Figure 8B:
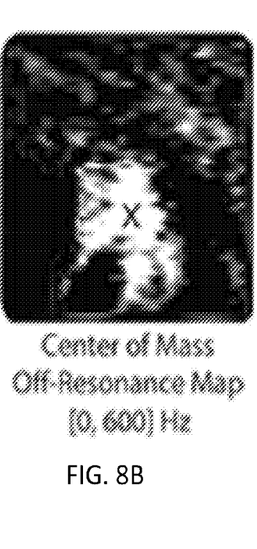
Figure 8C:
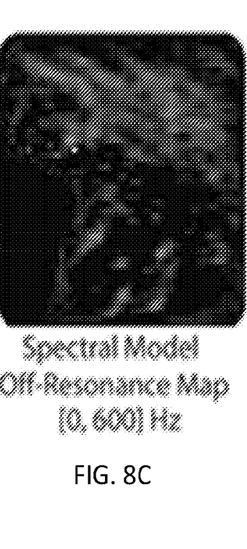
Figure 8D:
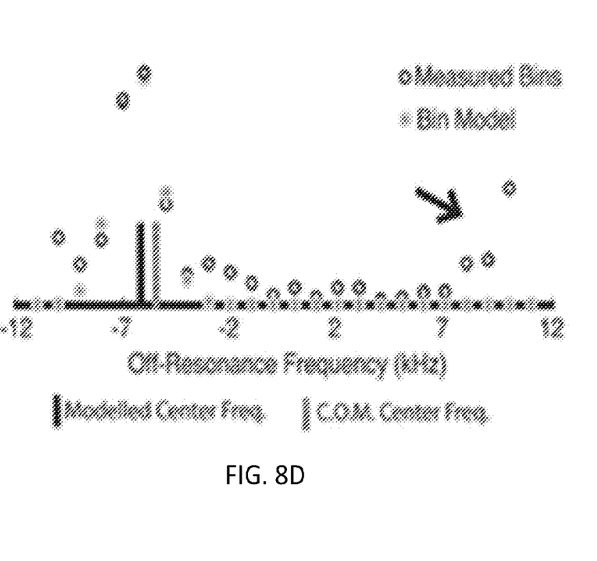

FIGS. 8A to 8D compare two off-resonance mapping methods and highlight the advantage of model-based 3D-MSI off-resonance mapping. A selected 3D-MSI in FIG. 8A shows a region of suspected metallosis. The background-removed off-resonance map computed with the conventional center-of-mass (COM) method of FIG. 8B indicates a large region of potential metallosis. However, the model-based residual map, as outlined above in association with block 108 of FIG. 1, shows far muted off-resonance signature. When examining the MSI spectral profile in the indicated position (X in COM map of FIG. 8B), a region of unanticipated elevated signal is seen in far off-resonant bins (arrow in FIG. 8D). This elevated signal, which is suspected to be caused by image ghosting artifacts in the off-resonant bins, slightly shifts the COM off-resonance estimate. When the model-based algorithm is utilized, the computed model is not impacted by the false magnitude elevations of the distant off-resonant bins. The ghosting artifacts of off-resonant bins in the lower signal region of suspected metallosis would have generated a false positive mScore in this case using the COM field map. The model-based approach thus reduces this risk of false-positive findings.

The choice of field mapping algorithm can be consequential in the elimination of false positive mScores across the control analysis cohort. Using the COM off-resonance mapping method, 25% of the 16 control cases yielded significant false positives (mean mScore=1.79). When applying the presented spectral modelling approach, all 16 control cases properly yielded null mScores.

Figure 9A:
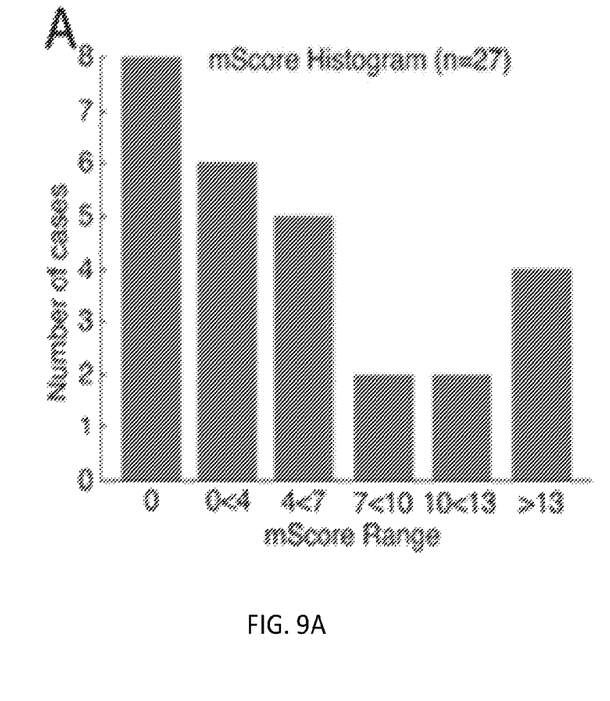
FIG. 9A to FIG. 9B show examples of mScores computed for a cohort of subjects as well as the correlation with histologic necrosis scores.
Figure 9B:
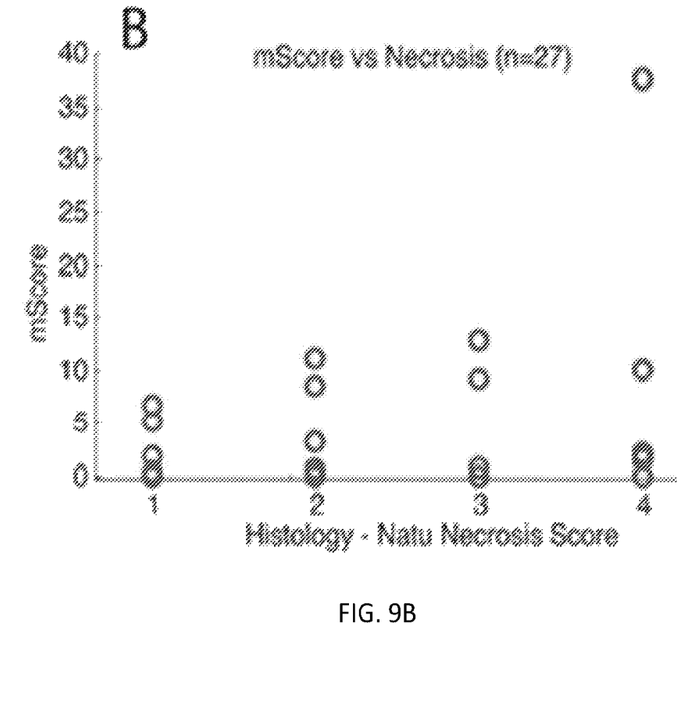

FIGS. 9A-9B demonstrate preliminary results from another proof of concept study. FIG. 9A provides a histogram of the mScores computed across the symptomatic cohort of six (6) subjects. The variety of scores is substantially distributed, with a mean of 4.4 and standard deviation of 8.8. While variations of magnetic susceptibility in different alloys of cobalt chromium could explain some of this variation, the different alloys of cobalt chromium used by implant manufacturers can vary by only roughly 30%. The far more extreme variation seen the mScore analysis is therefore more indicative of the differing concentrations and volumes of metallic wear products. FIG. 9B displays a plot of this mScore versus Natu necrosis score trend.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A method for determining metallic particle deposition in tissues near metallic implants using magnetic resonance imaging (Mill) data, the method comprising:
    accessing MM data acquired from a joint area that has received a replacement implant, the Mill data including a series of spatially mapped spectral data points, each at a particular offset frequency;
    generating Mill images of the joint area from the MM data;
    receiving information encoding a region of interest that encompasses a suspected metal particle deposition area over at least one of the Mill images generated from the MM data;
    constructing magnetic field maps using the Mill data, each magnetic field map representing off-resonance frequency shifts over the joint area;
    forming a tissue mask by examining a spectral integrity of the series of spatially mapped spectral data points to determine spatial areas that correspond to tissue;
    removing a background of off-resonance field inhomogeneity from the magnetic field map such that the region of interest is free from off-resonance field inhomogeneity caused by the implant itself;
    identifying voxels from the magnetic field maps with the background of off-resonance field inhomogeneity removed, the voxels defined over a first dimension of offset frequencies and a second dimension of voxel sizes; and
    computing a quantitative by combining information from the identified voxels according to both the first dimension and the second dimension.

2. The method of claim 1, wherein the MM data includes a series of three-dimensionally encoded spectral volumes, each spectrum volume corresponding to a particular offset frequency, and the spectrum volumes acquired with overlapping offset frequencies.

3. The method of claim 1, wherein the MRI data includes a series of two-dimensionally encoded spectrum slice sets, each spectrum slice set corresponding to a particular offset frequency, and the spectrum slice sets acquired with overlapping offset frequencies.

4. The method of claim 1, wherein constructing the magnetic field maps comprises: constructing the magnetic field maps by fitting the series of spatially mapped spectral data points against a model that describes a radiofrequency spectral profile applied when acquiring the MRI data.

5. The method of claim 4, wherein fitting the series of spectral data points comprises:
    fitting spectral profiles of each spatial quantum of the series of spatially mapped spectral data points against the model, the model comprising parameters that includes an offset frequency for each pixel of the constructed magnetic field map.

6. The method of claim 1, wherein constructing the magnetic field maps is based on a difference in phase information from the Mill data acquired with different echo times.

7. The method of claim 1, wherein examining the spectral integrity of the series of spatially mapped spectral data points comprises:
quantifying the spectral integrity by computing a ratio of a cumulative highest magnitude of a first number of spectrum volumes to a sum of a second number of spectrum volumes, wherein the first number and the second number jointly represent a total number of the spectrum volumes.

8. The method of claim 1, further comprising:
applying the tissue mask to the magnetic field maps prior to removing the background of off-resonance field inhomogeneity.

9. The method of claim 1, wherein computing the quantitative Currently Amended comprises applying a nonlinear weighting to sum information from the voxels in both the first dimension and the second dimension.

10. The method of claim 1, wherein computing the quantitative Currently Amended comprises applying a linear weighting to sum information from the voxels in both the first dimension and the second dimension.

11. A system for determining metallic particle deposition in tissues near metallic implants using magnetic resonance imaging (Mill) data, the system comprising:
an Mill scanner system configured to acquire Mill data from a joint area that has received a replacement implant, the Mill data including a series of spatially mapped spectral data points, each at a particular offset frequency;
a data processing system in communication with the MM scanner system, the data processing system comprising at least one processor configured to perform operations of:
accessing the Mill data acquired from the joint area;
generating Mill images of the joint area from the MM data;
receiving information encoding a region of interest that encompasses a suspected metal particle deposition area over at least one of the Mill images generated from the Mill data;
constructing magnetic field maps using the Mill data, each magnetic field map representing off-resonance frequency shifts over the joint area;
forming a tissue mask by examining a spectral integrity of the series of spatially mapped spectral data points to determine spatial areas that correspond to tissue;
removing a background of off-resonance field inhomogeneity from the magnetic field map such that the region of interest is free from off-resonance field inhomogeneity caused by the implant itself;
identifying voxels from the magnetic field maps with the background of off-resonance field inhomogeneity removed, the voxels defined over a first dimension of offset frequencies and a second dimension of voxel sizes; and
computing a quantitative value by combining information from the identified voxels according to both the first dimension and the second dimension.

12. The system of claim 11, wherein the MRI data includes a series of three-dimensionally encoded spectral volumes, each spectrum volume corresponding to a particular offset frequency, and the spectrum volumes acquired with overlapping offset frequencies.

13. The system of claim 11, wherein the MM data includes a series of two-dimensionally encoded spectrum slice sets, each spectrum slice set corresponding to a particular offset frequency, and the spectrum slice sets acquired with overlapping offset frequencies.

14. The system of claim 11, wherein constructing the magnetic field maps comprises: constructing the magnetic field maps by fitting spatially mapped spectral data points against a model that describes a radiofrequency spectral profile applied when acquiring the Mill data.

15. The system of claim 14, wherein fitting the series of three-dimensionally encoded spectral volumes comprises:
fitting spectral profiles of each spatial quantum of the series of spatially mapped spectral data points against the model, the model comprising parameters that includes an offset frequency for each pixel of the constructed magnetic field map.

16. The system of claim 11, wherein constructing the magnetic field maps is based on a difference in phase information from the Mill data acquired with different echo times.

17. The system of claim 11, wherein examining the spectral integrity of the series of spatially mapped spectral data points comprises:
quantifying the spectral integrity by computing a ratio of a cumulative highest magnitude of a first number of spectrum volumes to a sum of a second number of spectrum volumes, wherein the first number and the second number jointly represent a total number of the spectrum volumes.

18. The system of claim 11, wherein the data processing system is further configured to perform operations of:
applying the tissue mask to the magnetic field maps prior to removing the background of MRI field inhomogeneity.

19. The system of claim 11, wherein computing the quantitative value comprises applying a nonlinear weighting to sum information from the voxels in both the first dimension and the second dimension.

20. The system of claim 11, wherein computing the quantitative value comprises applying a linear weighting to sum information from the voxels in both the first dimension and the second dimension.

* * * * *